United States Patent
Kanazawa et al.

(10) Patent No.: US 7,819,524 B2
(45) Date of Patent: Oct. 26, 2010

(54) OPTOTYPE PRESENTING APPARATUS

(75) Inventors: Yuichiro Kanazawa, Okazaki (JP); Toshiya Kobayashi, Kariya (JP)

(73) Assignee: Nidek Co., Ltd., Gamagori-shi (JP)

( * ) Notice: Subject to any disclaimer, the term of this patent is extended or adjusted under 35 U.S.C. 154(b) by 139 days.

(21) Appl. No.: 11/819,267

(22) Filed: Jun. 26, 2007

(65) Prior Publication Data

US 2008/0002153 A1   Jan. 3, 2008

(30) Foreign Application Priority Data

Jun. 29, 2006   (JP) ............................... 2006-180486

(51) Int. Cl.
*A61B 3/00* (2006.01)
*A61B 3/08* (2006.01)
*A61B 3/02* (2006.01)

(52) U.S. Cl. ...................... 351/201; 351/200; 351/222; 351/239; 351/237; 351/244

(58) Field of Classification Search ................. 351/233, 351/246, 205, 222, 239, 201, 237, 244
See application file for complete search history.

(56) References Cited

U.S. PATENT DOCUMENTS

| | | | | |
|---|---|---|---|---|
| 2,238,207 A | * | 4/1941 | Ames, Jr. et al. ............ 351/211 |
| 4,239,351 A | * | 12/1980 | Williams et al. ............ 351/243 |
| 5,026,151 A | * | 6/1991 | Waltuck et al. ............. 351/246 |
| 5,121,981 A | | 6/1992 | Waltuck et al. |
| 5,880,814 A | | 3/1999 | McKnight et al. |
| 5,929,972 A | * | 7/1999 | Hutchinson ................. 351/237 |
| 6,425,665 B2 | | 7/2002 | Hayashi et al. |
| 7,233,312 B2 | * | 6/2007 | Stern et al. .................. 351/200 |
| 2001/0043309 A1 | * | 11/2001 | Hayashi et al. ............. 351/243 |
| 2002/0047997 A1 | | 4/2002 | Hayashi et al. |

FOREIGN PATENT DOCUMENTS

| | | |
|---|---|---|
| DE | 100 07 020 A1 | 8/2001 |
| GB | 2 031 699 A | 4/1980 |
| JP | A 2006-42978 | 2/2006 |
| WO | WO 02/076301 A1 | 10/2002 |

\* cited by examiner

*Primary Examiner*—Darryl J Collins
*Assistant Examiner*—Zachary Wilkes
(74) *Attorney, Agent, or Firm*—Oliff & Berridge, PLC

(57) ABSTRACT

An optotype presenting apparatus for presenting an optotype to be used for testing a visual function of an eye of an examinee, the apparatus comprises: a display unit including a memory in which a plurality of optotypes is stored and a display on which at least one of the stored optotypes is displayed; an operation unit by which at lest one of the stored optotypes to be displayed on the display is selected; a pilot lamp placed to be visible by the examinee who is in front of the display; and a control unit which turns on the pilot lamp when the display unit is powered on and the display is in an off-state, and turns off the pilot lamp when the display unit is powered on and the display is in an on-state.

2 Claims, 5 Drawing Sheets

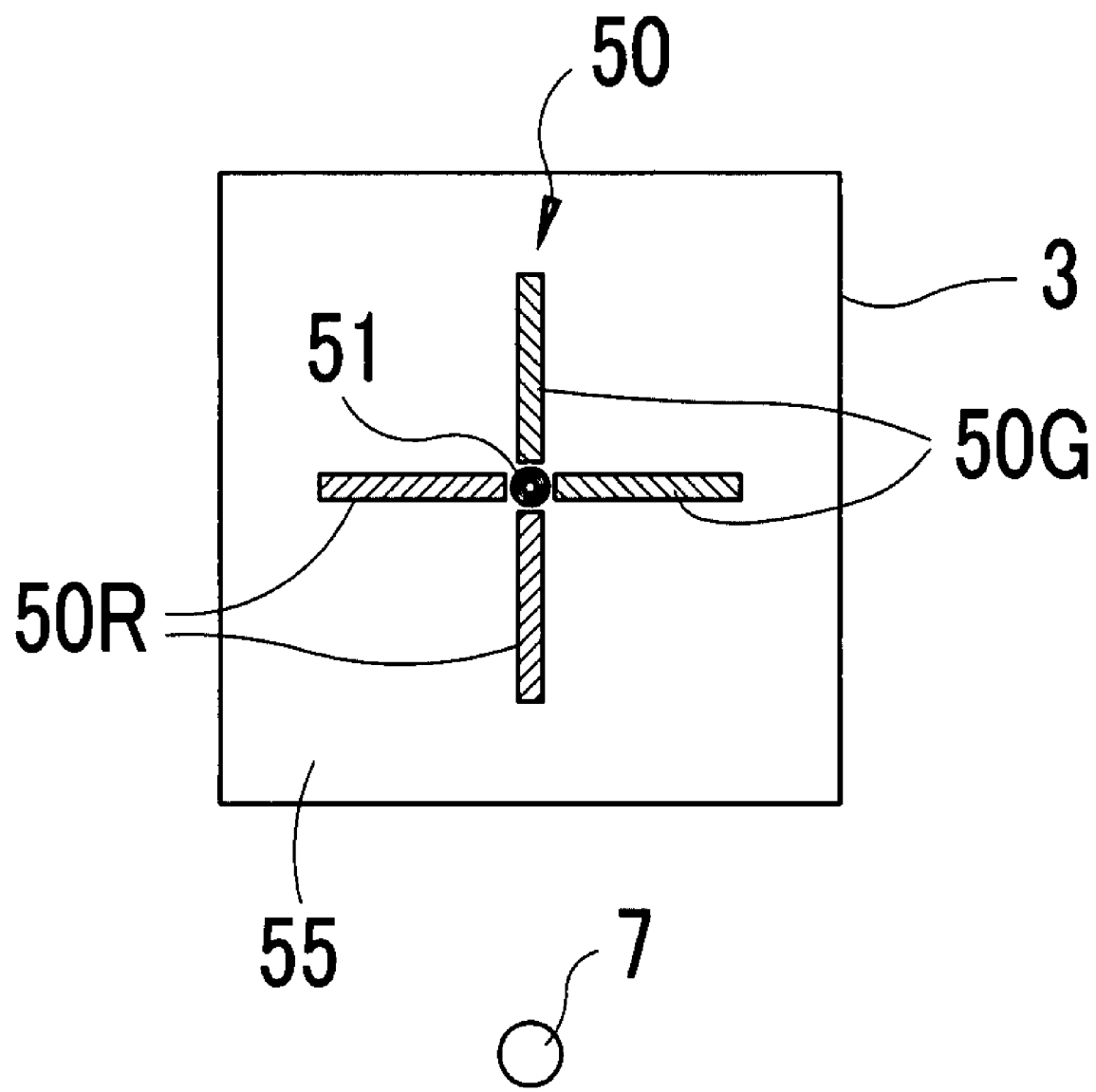

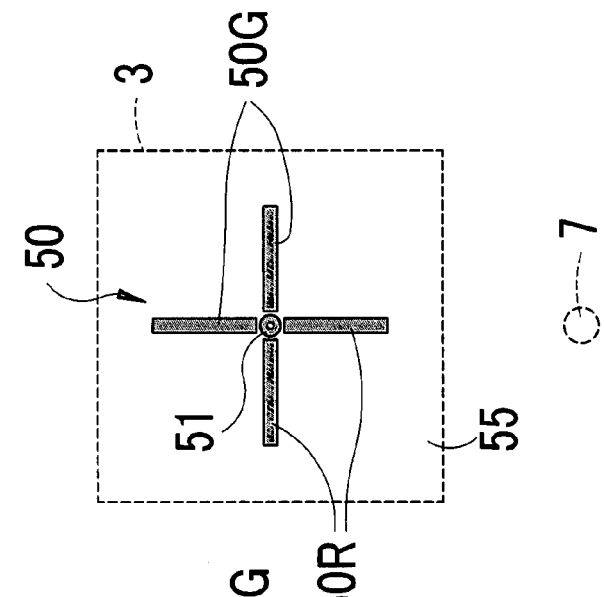
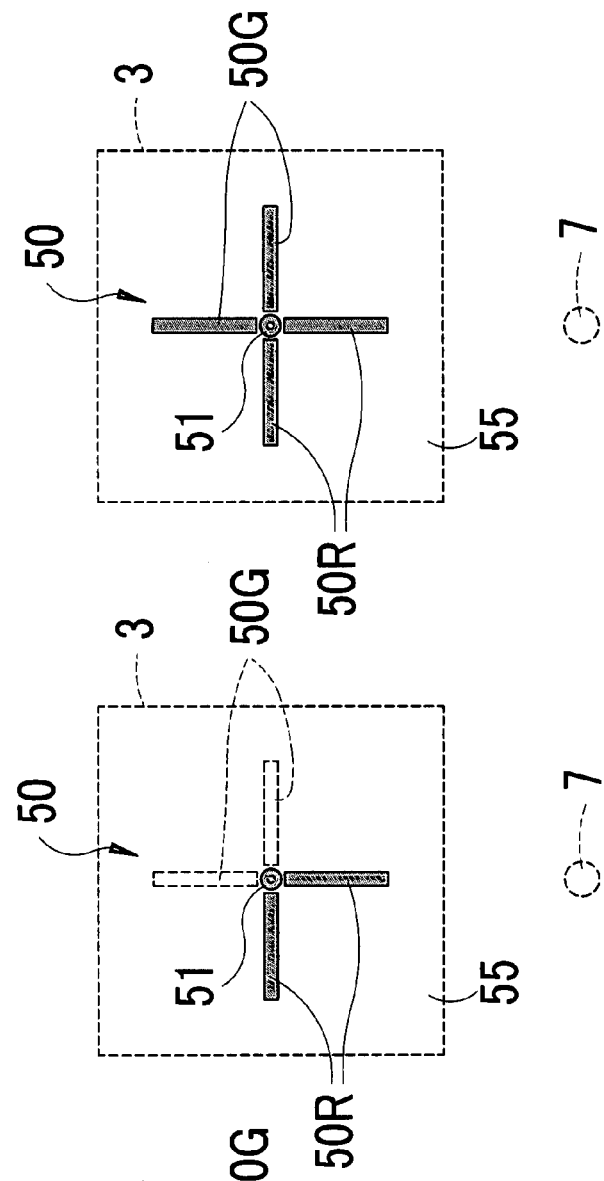
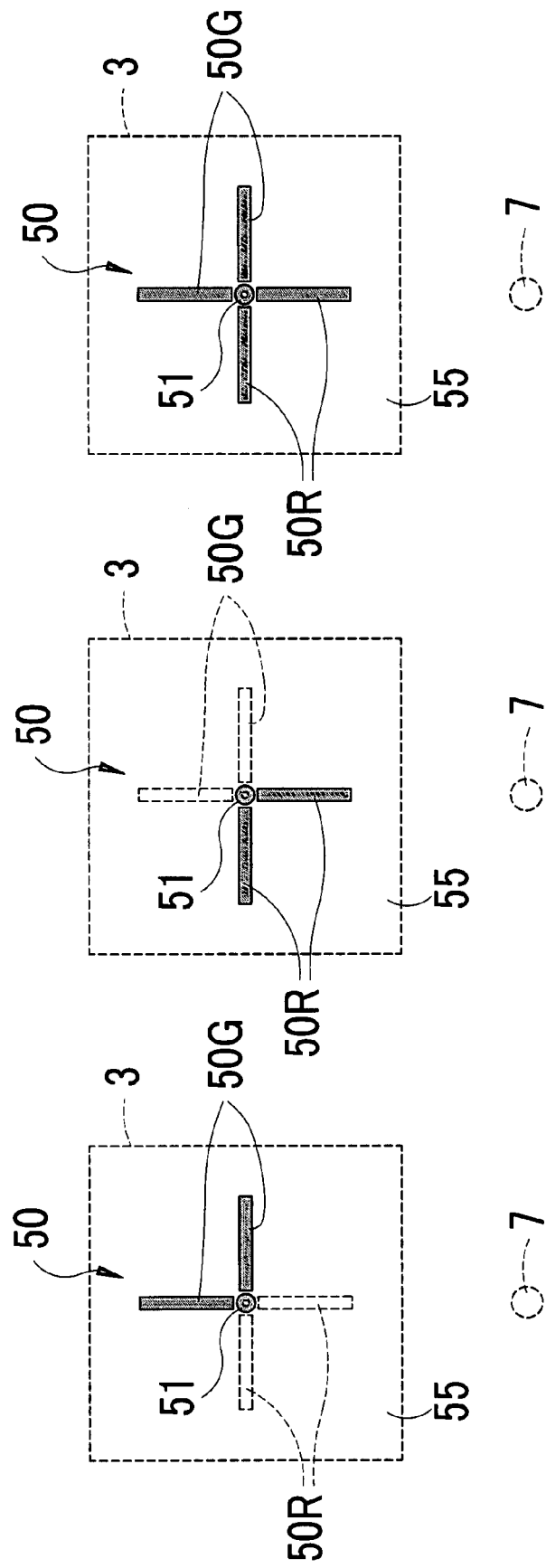

OPTOTYPE PRESENTING APPARATUS

BACKGROUND OF THE INVENTION

1. Field of the Invention

The present invention relates to an optotype presenting apparatus arranged to present a test optotype for testing a visual function of an examinee's eye.

2. Description of Related Art

An optotype presenting apparatus arranged to display vision test optotypes (charts) on a display such as a liquid crystal display and present the optotype(s) to examinee's eyes has ever been known (for example, see Jpn. unexamined patent publication No. 2006-42978). The optotype presenting apparatus of this type is located in use at a 5 m distance or others for a far vision test.

Meanwhile, an electrically-operated apparatus is usually provided with a pilot lamp (an indication light) for indicating an energized state of the apparatus to a user. On the other hand, a trend in a display-type optotype presenting apparatus is shifting towards a small-size and low-profile design.

However, as a housing of the apparatus is smaller in size and profile, the pilot lamp is placed closer to the display. When the pilot lamp lights up near an optotype displayed on the display, examinee's attention tends to be distracted from the optotype. This case is likely to cause a decrease in test accuracy and an increase in test time. In a test in a dark room, particularly, the light of the pilot lamp is conspicuous. Especially during a binocular vision test, the pilot lamp placed close to the optotype is likely to act as a fusion stimulus.

BRIEF SUMMARY OF THE INVENTION

The present invention has an object to provide an optotype presenting apparatus that allows easy visual check of an energized state of the apparatus as conventionally and that is scarcely influenced by a pilot lamp particularly during a binocular vision test, thereby allowing the test to be executed smoothly.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an optotype presenting apparatus for presenting an optotype to be used for testing a visual function of an eye of an examinee, the apparatus comprising: a display unit including a memory in which a plurality of optotypes is stored and a display on which at least one of the stored optotypes is displayed; an operation unit by which at lest one of the stored optotypes to be displayed on the display is selected; a pilot lamp placed to be visible by the examinee who is in front of the display; and a control unit which turns on the pilot lamp when the display unit is powered on and the display is in an off-state, and turns off the pilot lamp when the display unit is powered on and the display is in an on-state.

According to another aspect, the present invention provides an optotype presenting apparatus for presenting an optotype to be used for testing a visual function test of an eye of an examinee, the apparatus comprising: a display; and a pilot lamp placed to be visible by the examinee who is in front of the display, the pilot lamp being arranged to be turned on when the apparatus is powered on and be turned off when the apparatus is powered off, wherein the pilot lamp is turned off when the optotype is displayed on the display even though the apparatus is powered on.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings,

FIG. 3 is a view to explain a heterophoria test;

FIGS. 4A to 4C are views to explain how an optotype for the heterophoria test appears.

DETAILED DESCRIPTION OF THE PREFERRED EMBODIMENTS

Figure 1:
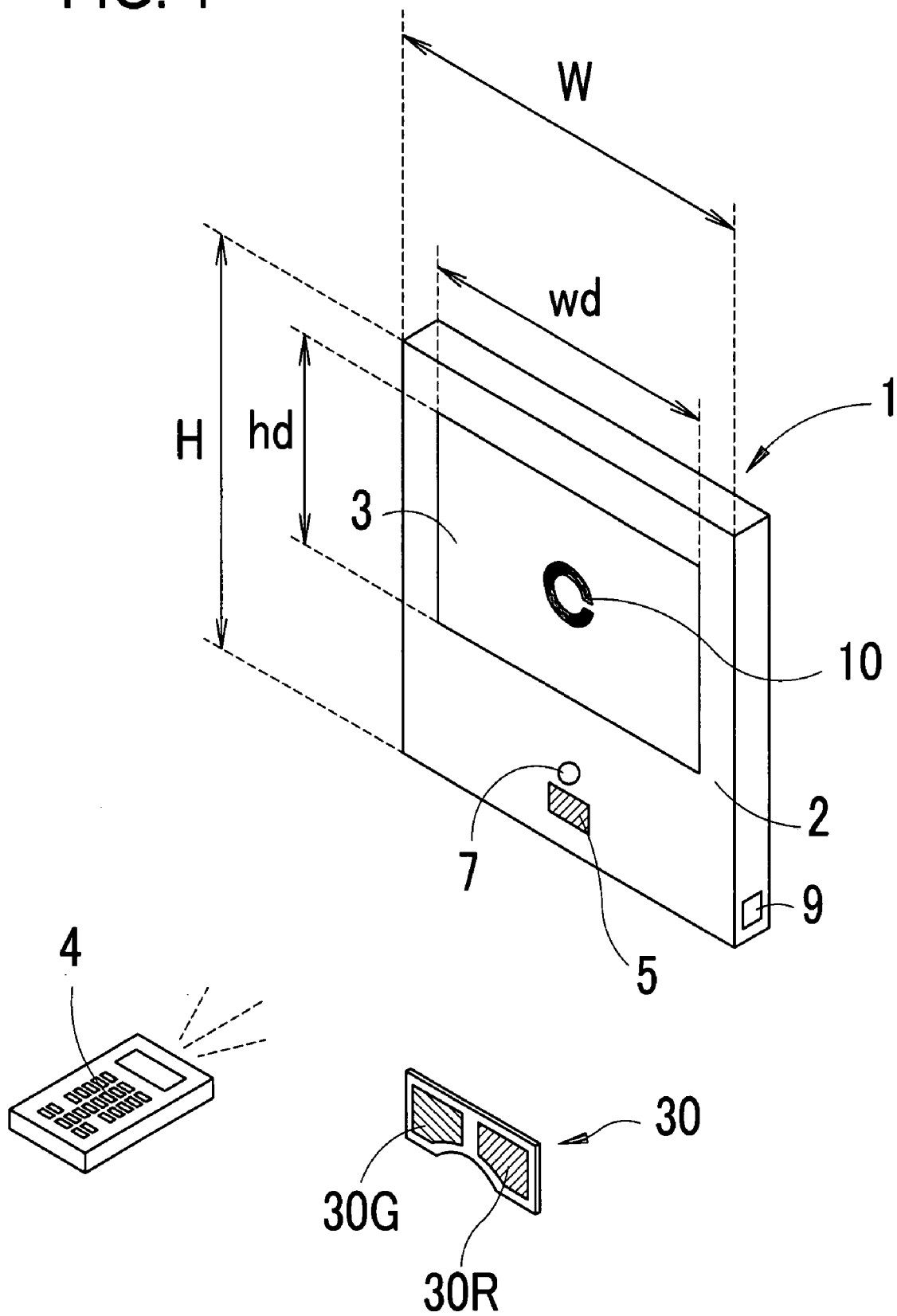
FIG. 1 is an external view of an optotype presenting apparatus of a preferred embodiment of the present invention.

A detailed description of a preferred embodiment of the present invention will now be given referring to the accompanying drawings. FIG. 1 is an external view of an optotype presenting apparatus of the present embodiment.

At a front surface of a housing 2 of the optotype presenting apparatus 1, a color liquid crystal display (LCD) 3 is provided to present optotypes. This display 3 used in the present embodiment has a 19-inch size to display a predetermined size of a test optotype 10 even where the apparatus is placed at a distance for a far vision test, e.g., 5 m. The housing 2 is designed to have a height H smaller than twice the height "hd" of the display 3 in order to minimize the area of the front surface other than the display 3. A width W of the housing 2 is also determined to be smaller than twice the width "wd" of the display 3. Further, the housing 2 is designed to have a thickness of as small as about 5 cm for allowing wall-mounted use.

At a lower part of the front surface of the housing 2, a receiver 5 which receives a communication signal of infrared light from a remote controller 4 is provided as well as a pilot lamp 7 for indicating the energized state of the apparatus to a user. The position of the pilot lamp 7 is not limited to the front surface of the housing 2, but it is preferably a position where an examiner who is at the distance for far vision test, in front of the housing 2, can see the pilot lamp 7. A power switch 9 is provided on the side of the housing 2. The optotype 10 to be displayed on the display 3 can be changed by operation of the remote controller 4. When a single letter optotype 10 is selected, the optotype 10 is displayed in almost the center of the display 3. Red-green spectacles 30 have a red filter 30R for a right eye and a green filter 30G for a left eye. Using the red-green spectacles 30, a binocular vision test on the examinee is carried out.

Figure 2:
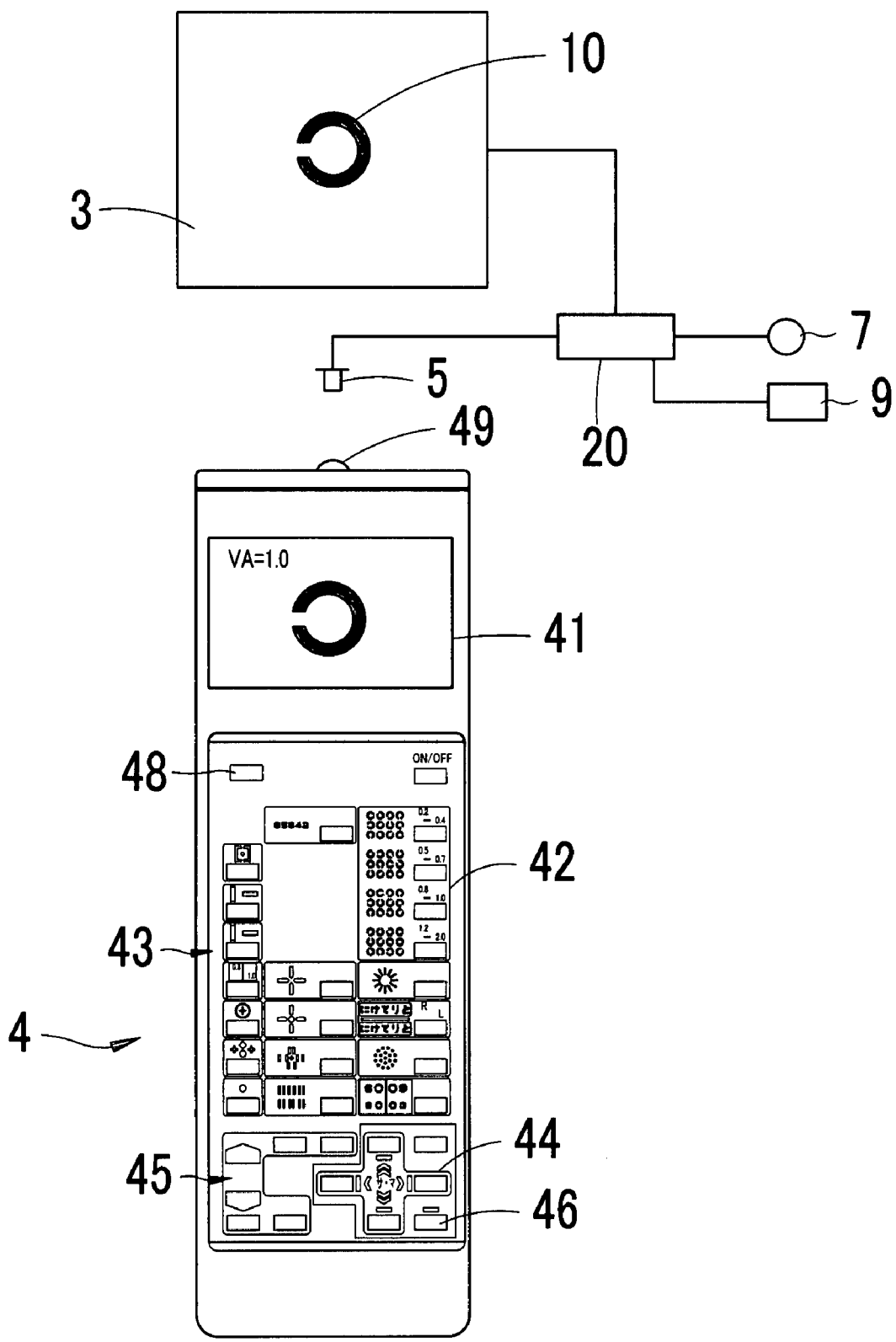
FIG. 2 is a schematic control block diagram.

FIG. 2 is a schematic control block diagram of the optotype presenting apparatus of the present embodiment. The display 3, the receiver 5, and the pilot lamp 7 are connected to a control unit 20. The control unit 20 internally contains a memory which stores various figures of optotypes, a decoder circuit which decodes command signals from the remote controller 4, and others.

The remote controller 4 includes a plurality of buttons to be used for operating an apparatus main unit and a liquid crystal display 41 which displays conditions selected with the buttons. Upon press of a button(s) of a vision optotype selector switch section 42 corresponding to a visual acuity, an optotype corresponding to the visual acuity is displayed on the display 3. At this time, the same optotype is also displayed on the display 41 as well as the visual acuity. A test optotype selector switch section 43 is operated to display optotypes for various visual function tests such as a red-green test, a cross-cylinder test, and a binocular vision test. An orientation selecting button 44 and a visual acuity up/down button 45 are pressed to change the orientation of the currently displayed optotype and to increase or decrease the visual acuity. An image display button 46 is pressed to display an image previously stored in the control unit 20.

To establish a power-saving mode, a power-saving mode button 48 is pressed. When the button 48 is pressed while an optotype is appearing on the display 3, the screen (backlight) of the display 3 is turned off by the control unit 20, whereas the apparatus 1 is maintained in the energized state (that is, power is ON). Switching to the power-saving mode is not only caused by operation of the remote controller 4 by the examiner but also can be conducted automatically by the control unit 20 even when no operation signal is transmitted to the apparatus 1 for a fixed time. This fixed time in this case can be changed variously by the examiner. A transmitter 49 transmits a command signal from the remote controller 4.

With reference to the apparatus having the above configuration, characteristic operations of the present invention will be explained. When the power switch 9 is turned ON, supplying power to the apparatus 1, a predetermined screen or an initial optotype is displayed on the display 3 under control of the control unit 20. Here, the pilot lamp 7 serves to indicate the energized state of the apparatus. While the optotype or others (at least an optotype for the binocular vision test) is displayed on the display 3, the pilot lamp 7 remains unlit under the control of the control unit 20. Even where the pilot lamp 7 is in an off-state, the energization of the apparatus is obvious from an on-state of the display 3 and thus no practical problem is caused.

The examiner manipulates various buttons on the remote controller 4 to perform a visual function test by switching the test optotypes. The examinee who stands apart from the apparatus 1 by a predetermined test distance gazes at the optotype 10 displayed on the display 3. Even where the pilot lamp 7 is arranged in such a position as to be seen by the examinee who is in front of the display 3, it does not interfere with the attention of the examinee who looks at the optotype because the pilot lamp 7 remains off. This makes it possible to perform a test accurately and smoothly. In particular, the lamp 7 should be conspicuous if remains on during a test in a dark room. However, the pilot lamp 7 remains off (including a case where the light intensity of the lamp 7 is so reduced as to be unnoticeable) during the test and thus will not interfere with the test. A sensor for detecting the light intensity to determine whether it corresponds to a dark room may be provided to turn off the pilot lamp only during a test in a dark room. Alternatively, a selector switch may be added to the remote controller 4.

An example of a test to be performed by displaying optotypes for the binocular vision test will be explained. FIG. 3 is a view for explaining a heterophoria test, showing a display screen of the display 3 which appears when an optotype 50 for the heterophoria test with a fusion optotype is selected. The test optotype 50 is displayed on the display 3 at the press of a selection switch for identifying "Heterophoria" of a function test optotype selector switch section. A back screen 55 is displayed in white. Presented figures 50G (a first figure) are displayed in green as an optotype to be presented to only a right eye through the red filter 30R. Presented figures 50R (a second figure) are displayed in red as an optotype to be presented to only a left eye through the green filter 30G. A fusion optotype 51 is displayed in black to be presented to both eyes at the same time. The figures and their colors to be displayed on the screen of the display 3 are controlled by the control unit 20.

FIGS. 4A to 4C are views to explain how the heterophoria test optotype 50 with the fusion optotype appears. The optotype 50 appears as in FIG. 4A by the right eye wearing the red-green spectacles 30. The right eye looks at the display 3 through the red filter 30R and thus the back screen 55 appears to be red. The red presented figures 50R are seen through the red filter 30R and thus they apparently blend into the back screen 55 (their shapes become unrecognizable). The presented figures 50G having no red-color component are recognized as black figures by the examinee. At this time, the fusion optotype 51 appears in black as before.

On the other hand, the same phenomenon also occurs in the left eye as in the right eye (see FIG. 4B). The left eye looks at the display 3 through the green filter 30G. Accordingly, the back screen 55 appears to be green and the presented figures 50G also apparently blend into the back screen 55 (their shapes become unrecognizable).

As above, the images to be seen by the right eye and the left eye are different from each other. The heterophoria of the examinee is examined by use of the fusion optotype 51. In the case of an emmetropic eye, as shown in FIG. 4C, the presented figures 50R and the presented figures 50G appear without displacement. In the case where the examinee's eye has horizontal heterophoria, the presented figures 50R and the presented figures 50G appear to be displaced horizontally.

When the pilot lamp 7 remains on in such heterophoria test, it may act as a fusion stimulus which makes the examinee confuse it with the fusion optotype 51. If an area of a frame portion of the housing 2 other than the display 3 is smaller as in the present apparatus, the position of the pilot lamp 7 is closer to the test optotype 50. As the pilot lamp 7 is placed closer to the test optotype 50 and its luminance is higher, the pilot lamp 7 is recognized more conspicuously. Particularly, the pilot lamp 7 is likely to act as a stimulus during a test in a dark room. Due to the existence of the pilot lamp 7, the examinee tends to fall into a lapse of attention. If the pilot lamp 7 remains off during a test, on the other hand, it will not interfere with the test.

Figure 5:
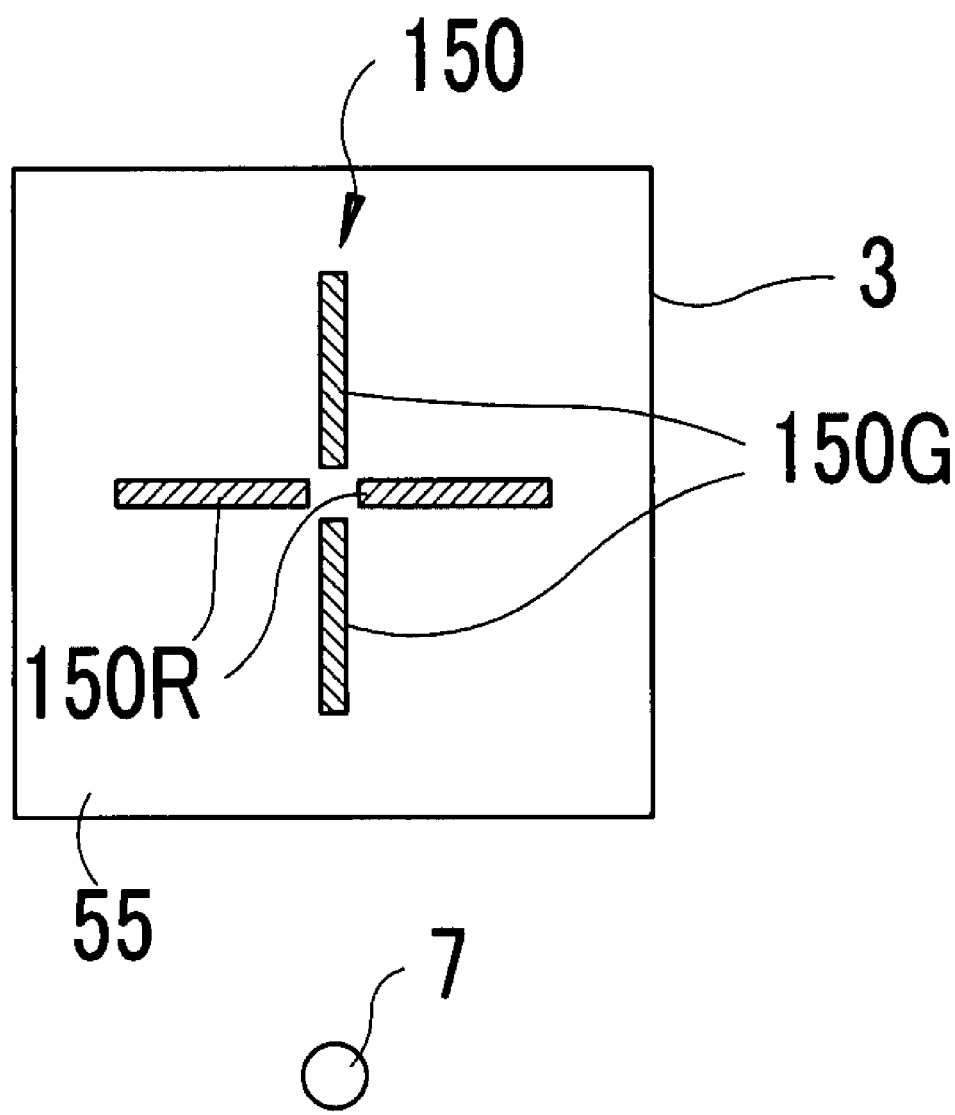
FIG. 5 is an explanatory view of another example of the heterophoria test.

FIG. 5 shows an example of an optotype for a heterophoria test, which does not include the fusion optotype included in the optotype in FIG. 3. In this optotype, two vertically linear figures 150G (a first figure) are displayed in green and two horizontally linear figures 150R (a second figure) are displayed in red. As mentioned above, the red-green spectacles 30 are worn in front of the examinee's eyes and the heterophoria test is performed. This heterophoria test optotype 150 does not include the fusion optotype 51 shown in FIG. 3, so that the heterophoria test can be conducted accurately. Here, if the pilot lamp 7 remains on, it may act as a fusion stimulus and disturb an exact measurement of an amount of heterophoria. With the present apparatus in which the pilot lamp 7 remains off during the test, the heterophoria test can be performed more accurately.

After completion of the test, if no operation signal is input from the remote controller 4 for a fixed time (e.g. 5 min.), or, if an operation signal is input with the power-saving mode button 48, the control unit 20 establishes the power-saving mode, turning off the display 3 and turning on the pilot lamp 7. When the display 3 is turned off, the energized state of the apparatus cannot be recognized. However, with the lighted pilot lamp 7, the examiner can readily recognize the energized state of the apparatus even where he/she is at a distance for a far vision test. And if the examiner wants to restart the test, he/she has only to press any switch on the controller 4. Therefore the power-saving mode is released, and the test can smoothly restarted by the control unit 20.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An optotype presenting apparatus for presenting an optotype to be used for testing a visual function of an eye of an examinee, the apparatus comprising:

a display unit including:

a display on which an optotype is selectively displayed, the display being placed at a front surface of the display unit;

a power switch placed in the display unit, by which the display unit is powered on and powered off;

a pilot lamp placed at a position of the front surface around the display unit, for indicating a powered-on-state of the display unit by turning on the pilot lamp; and a control unit in the display unit, which controls the display unit including the display and the pilot lamp and has a memory in which a plurality of optotypes including an optotype for red-green test and an optotype with a fusion stimulus pattern are stored as image data; and a remote controller including a plurality of buttons including an optotype selector switch section by which at least one of the stored optotypes to be displayed on the display is selected;

wherein the control unit turns on the pilot lamp when the display unit is powered on, turns off the pilot lamp during an examination in which the selected optotype is displayed on the display when the display unit is powered on so as to prevent the pilot lamp from interfering with the examinee's attention with respect to the displayed optotype, returns to a turn-on-state of the pilot lamp when no operating signal is given for a fixed time after the examination is completed or when a power-saving signal is given, and returns to a turn-off-state of the pilot lamp when the display unit is powered off.

2. The optotype presenting apparatus according to claim 1, wherein the control unit turns off the pilot lamp when the optotype with the fusion stimulus pattern is displayed on the display.

* * * * *